US009393242B2

(12) United States Patent
Eilat

(10) Patent No.: US 9,393,242 B2
(45) Date of Patent: *Jul. 19, 2016

(54) COMPOSITIONS FOR TREATMENT OF EAR DISORDERS AND METHODS OF USE THEREOF

(75) Inventor: Eran Eilat, Herzliya (IL)

(73) Assignee: OTIC PHARMA LTD., Ariel (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/220,350

(22) Filed: Aug. 29, 2011

(65) Prior Publication Data

US 2011/0311462 A1 Dec. 22, 2011

Related U.S. Application Data

(63) Continuation of application No. 10/582,712, filed as application No. PCT/IL0204/001122 on Dec. 12, 2004, now Pat. No. 8,030,362.

(60) Provisional application No. 60/530,014, filed on Dec. 12, 2003, provisional application No. 60/587,510, filed on Jul. 14, 2004.

(51) Int. Cl.
*A61K 9/12* (2006.01)
*A61F 9/02* (2006.01)
*A61K 31/19* (2006.01)
*A61K 31/495* (2006.01)
*A61K 9/00* (2006.01)

(52) U.S. Cl.
CPC ............ *A61K 31/495* (2013.01); *A61K 9/0046* (2013.01); *A61K 9/122* (2013.01); *Y10S 514/945* (2013.01); *Y10S 514/956* (2013.01)

(58) Field of Classification Search
CPC ... A61K 31/495; A61K 9/0046; A61K 9/122; Y10S 514/945; Y10S 514/956
See application file for complete search history.

(56) References Cited

U.S. PATENT DOCUMENTS

| 4,241,048 | A | 12/1980 | Durbank |
| 4,305,936 | A | 12/1981 | Klein |
| 4,915,934 | A | 4/1990 | Tomlinson |
| 5,322,683 | A | 6/1994 | Mackles |
| 5,369,131 | A | 11/1994 | Poli et al. |
| 5,393,528 | A | 2/1995 | Staab |
| 5,397,564 | A | 3/1995 | Seki et al. |
| 5,401,741 | A | 3/1995 | Sato et al. |
| 5,502,076 | A | 3/1996 | Dixit et al. |
| 5,529,782 | A | 6/1996 | Staab |
| 5,635,469 | A | 6/1997 | Fowler et al. |
| 5,679,665 | A | 10/1997 | Bergamini et al. |
| 5,697,532 | A | 12/1997 | Wilder et al. |
| 5,744,166 | A | 4/1998 | Illum |
| 5,759,520 | A | 6/1998 | Sachetto |
| 5,843,930 | A | 12/1998 | Purwar et al. |
| 5,965,549 | A | 10/1999 | Purwar et al. |
| 6,030,931 | A | 2/2000 | Vinski et al. |
| 6,032,836 | A | 3/2000 | Hiscocks et al. |
| 6,126,920 | A | 10/2000 | Jones et al. |
| 6,238,650 | B1 | 5/2001 | Lapidot et al. |
| 6,258,374 | B1 | 7/2001 | Friess et al. |
| 6,284,804 | B1 | 9/2001 | Singh |
| D456,260 | S | 4/2002 | Boshuizen |
| 6,428,772 | B1 * | 8/2002 | Singh ................ A61K 8/22 424/401 |
| 6,521,213 | B1 * | 2/2003 | Mautone .................... 424/45 |
| 6,534,087 | B2 | 3/2003 | Busson et al. |
| 6,612,468 | B2 | 9/2003 | Pritchett et al. |
| 6,660,282 | B2 | 12/2003 | Crotty et al. |
| 6,702,155 | B1 | 3/2004 | Rebne |
| 6,730,288 | B1 | 5/2004 | Abram |
| 6,764,470 | B2 | 7/2004 | Dimick |
| 7,820,145 | B2 * | 10/2010 | Tamarkin ............. A61K 8/046 424/45 |
| 8,030,362 | B2 * | 10/2011 | Eilat ............................ 514/2.4 |
| 2002/0018812 | A1 | 2/2002 | Busson |
| 2002/0064541 | A1 | 5/2002 | Lapidot et al. |
| 2003/0178022 | A1 | 9/2003 | Davies et al. |
| 2004/0057922 | A1 | 3/2004 | Schmid et al. |
| 2005/0031547 | A1 | 2/2005 | Tamarkin et al. |

(Continued)

FOREIGN PATENT DOCUMENTS

| CA | 2527499 | 12/2004 |
| DE | 554349 | 7/1932 |

(Continued)

OTHER PUBLICATIONS

Ardizzone et al., "Mesalozine foam (Salofalk foam) in the treatment of active distal ulcerative colitis. A comparative trial vs. Salofalc enema. The SAF-3 study group" Ital J. Gastroenterol Hepatol 31:677-84 (1999) (Abstract).
Borelli et al., Creme or foam in pedal skin care: towards the ideal vehicle for urea used against dry skin, Int. J. Cosmet Sci 33:37-43 (2011).
Cortot et al., "Mesalamine foam enema vs. mesalamine liquid enema in active left-sided ulcerative colitis" Am J. Gastroenterpol 103(12):3106-14 (2008).

(Continued)

*Primary Examiner* — Mina Haghighatian
(74) *Attorney, Agent, or Firm* — Browdy and Neimark, PLLC.

(57) ABSTRACT

The present invention relates to compositions and methods useful for the treatment of ear disorders, administered to a treated ear in the form of a foam or a mousse. Administering a medicament in such forms will increase the residence time of the medicament in the ear canal, provide relatively uniform distribution of the composition, and can increase the penetration of the active pharmaceutical ingredient in the affected area, may release active substances slowly, enhance treatment effectiveness, increase compliance and is more convenient to use than currently available ear medications. The administration in the form of a foam or a mousse may preferably be provided as a metered dose, of a volume suitable to fill the ear canal.

13 Claims, 2 Drawing Sheets

(56) References Cited

U.S. PATENT DOCUMENTS

2008/0075670 A1  3/2008  Eilat
2012/0252720 A1  10/2012  Eilat

FOREIGN PATENT DOCUMENTS

| GB | 0933486 | | 8/1963 |
|---|---|---|---|
| WO | WO9603115 | * | 2/1996 |
| WO | 00/33775 | | 6/2000 |
| WO | WO 2004037225 A2 | | 5/2004 |

OTHER PUBLICATIONS

Farup et al., "Mesalazine suppositories versus hydrocortisone foam in patients with distal ulcerative colitis. A comparison of the efficacy and practicality of two topical treatment regiments." Scand J. Gastroenterol 30(2):164-170 (1995).
Franz "Bioavailability of clobetasol propionate in different vehicles." Skin Pharmacol Appl Skin Physiol, 16(4):212-216 (2003) (Abstract).
Gross et al., "Budesonide foam versus budesonide enema in active ulcerative proctitis and proctosigmoiditis" Aliment Pharmacol Ther 23:303-312 (2006).
Lucidarme et al., "Efficacy and tolerance of mesalazine suppositories vs. hydrocortisone foam in proctitis" Aliment Pharmacol Ther 11(2):335-340 (1997) (Abstract).
Ngo et al., "[5-aminosalycilic acid enema (Pentasa) versus hydrocortisone acetate foam (Proctocort) for the treatment of outbreaks of proctitis and cryptogenetic proctosigmoiditis. A comparative randomized multicentered trial]" Gastroenterol Clin Biol 16(6-7):558-563 (1992) (Abstract).
Ruddell et al., "Treatment of distal ulcerative colitis (proctosigmoiditis) in relapse: comparison of hydrocordisone enemas and rectal hydrocortisone foam" Gut, 21:885-889 (1980).
Somerville et al., "Effect of treatment on symptoms and quality of life in patients with ulcerative colitis: comparative trial of hydrocortisone acetate foam and prednisolone 21-phosphate enemas" British Medical Journal 291:866 (1985).
Tarpila et al., "Budesinide Enema in active hemorrhagic proctitis—a controlled trial against hydrocortisone foam enema" Aliment Pharmacol. Ther 8(6):591-595 (1994) (Abstract).
Woodford et al., "Bioavailability and activity of topical corticosteroids from a novel drug delivery system, the aerosol quick-break foam" J. Pharm Sci 66(1):99-103 (1977) (Abstract).
Marom et al., "Comparison of safety and efficacy of foam-based versus solution-based ciprofloxacin for acute otitis externa," Otolaryngology—Head and Neck Surgery, 143:492-499 (2010).
Hannley, M.T. et al., "Use of ototopical antibiotics in treating 3 common ear diseases", Otolaryngol Head Neck Surg, (2000), vol. 116, pp. 924-940.
Cortifoam, Drug information by Drug.com, Obtained online on Nov. 9, 2010.
Cortifoam, PDR 1995 Edition, pp. 1949-1950.
U.S. Appl. No. 60/492,385, filed Aug. 4, 2003, from prosecution history of U.S. Appl. No. 10/835,505, published as US2005/0031547.
U.S. Appl. No. 60/530,015, filed Dec. 16, 2003, from prosecution history of U.S. Appl. No. 10/835,505, published as US2005/0031547.
Scharfstein, M. "Spuman-Therapie der chronischen Otitiden, Monatsschrift Fuer Ohrenheilkunde Und Laryngo-Rhinologie" Österreichische Oto-Laryngologische Gesellschaft Wiener Gesellschaft Der Hals-Nasen-Ohren-Ärzte 67:978-981 (1993) article in German. translation not provided; but see accompanying IDS Supporting Communication for brief description of relevance.
Counterpart EP 04801606.7 Supplementary European Search Report dated Aug. 14, 2012.
Counterpart EP 04801606.7 communication from the examining division dated Nov. 6, 2012.
Counterpart CA 2548892 Office Action dated Nov. 25, 2010.
U.S. Appl. No. 10/582,712 Non-Final Rejection May 20, 2010.
U.S. Appl. No. 10/582,712 Final-Rejection Nov. 23, 2010.
U.S. Appl. No. 10/582,712 Advisory action Mar. 4, 2011.
Woodford et al., "Bioavailability and Activity of Topical Corticosteroids from a Novel Drug Delivery System, the Aerosol Quick-Break Foam" J. Pharmaceut. Sci, 66:99-103 (1977).
Tamarkin et al., "Formulating Topical Applications—a Practical Guide" Dayan N., ed., Chapter 9, pp. 233-260 (2013).

* cited by examiner

COMPOSITIONS FOR TREATMENT OF EAR DISORDERS AND METHODS OF USE THEREOF

FIELD OF THE INVENTION

The present invention relates to compositions and methods for the treatment of ear disorders, wherein the pharmacologically active agent is administered to a treated ear in a form selected from a foam and a mousse. The compositions and methods of administering a medicament in these forms provide accurate dosage volumes, increase the residence time of the medicament in the ear canal, enhance treatment effectiveness, increase compliance and are more convenient to use than currently available ear medications.

BACKGROUND OF THE INVENTION

Ear Structure

The ear, which is the organ of hearing and balance, consists of the outer, middle, and inner ear. The outer, middle, and inner ear function together to convert sound waves into nerve impulses that travel to the brain, where they are perceived as sound. The inner ear also helps to maintain balance.

Outer Ear

The outer ear consists of the external part of the ear (pinna or auricle) and the ear canal (external auditory meatus). The pinna consists of cartilage covered by skin and is shaped to capture sound waves and funnel them through the ear canal to the eardrum (tympanic membrane), a thin membrane that separates the outer ear from the middle ear.

Middle Ear

The middle ear consists of the eardrum and a small air-filled chamber containing a chain of three tiny bones (ossicles) that connect the eardrum to the inner ear. The ossicles are named for their shapes. The hammer (malleus) is attached to the eardrum. The Eustachian tube, a small tube that connects the middle ear with the back of the nose, allows outside air to enter the middle ear. This tube, which opens when a person swallows, helps maintain equal air pressure on both sides of the eardrum and prevents fluid from accumulating in the middle ear. If air pressure is not equal, the eardrum may bulge or retract, which can be uncomfortable and distort hearing. The Eustachian tube's connection with the middle ear explains why upper respiratory infections (such as the common cold), which inflame and block the Eustachian tube, can lead to middle ear infections or changes in middle ear pressure, resulting in pain.

Inner Ear

The inner ear (labyrinth) is a complex structure consisting of two major parts: the cochlea, the organ of hearing; and the vestibular system, the organ of balance. The vestibular system consists of the saccule and the utricle, which determine position sense, and the semicircular canals, which help maintain balance.

The cochlea, a hollow tube coiled in the shape of a snail's shell, is filled with fluid. Within the cochlea is the organ of Corti, which consists, in part, of about 20,000 specialized cells, called hair cells. These cells have small hairlike projections (cilia) that extend into the fluid. Sound vibrations transmitted from the ossicles in the middle ear to the oval window in the inner ear cause the fluid and cilia to vibrate. Hair cells in different parts of the cochlea vibrate in response to different sound frequencies and convert the vibrations into nerve impulses. The nerve impulses are transmitted along fibers of the cochlear nerve to the brain. Despite the protective effect of the acoustic reflex, loud noise can damage and destroy hair cells. Once a hair cell is destroyed, it does not appear to regrow. Continued exposure to loud noise causes progressive damage, eventually resulting in hearing loss and sometimes noise or ringing in the ears (tinnitus). The semicircular canals are three fluid-filled tubes at right angles to one another. The canals contain hair cells that respond to the movement of the fluid. If the semicircular canals malfunction, as may occur in an upper respiratory infection and other conditions both temporary and permanent, a person's sense of balance may be lost or a whirling sensation (vertigo) may develop.

Use of Ear Drops for the Treatment of Ear Disorders

Currently, ear care products (otic, ototopical agents) are administered to the treated subject in the form of drops. Generally, ear drops are based on antibiotic agents, antibacterial agents, antifungal agents, antiviral agents, steroid derivatives, anti-inflammatory agents, analgesic compounds or a mixture thereof. For example, initial therapy for acute otitis externa (AOE) is typically a combination consisting of neomycin, polymyxin B and a steroid (commercially available as for example, Cortisporin™) (Lee L, Steinberg I, Gill M A. Management of Ear Infections. Cal Parma 2001; Spring; 56-64). Current medications also include quinolone derivatives i.e. Ciprofloxacin 1% or Oflaxacin 0.3%. Other compositions of ear drops are further described in U.S. Pat. Nos. 5,401,741; 5,679,665; 5,965,549; and 5,843,930 the entire disclosures of which are hereby incorporated by reference.

Another common use of ear drops is for ear pain treatment. Ear pain (otalgia) can range from mild discomfort or a feeling of fullness to severe intense pain, and can be very unpleasant and even unbearable, especially in children. Usually, ear pain results from pathological conditions of the external or middle ear. Such pathological conditions, discussed lengthily above, may be caused by infection, trauma, or blockage of the ear. Briefly, common trauma may result by use of a cotton swab to clean the ear or as a result of sudden changes in pressure such as changes in altitude when flying or diving. Blockage of the ear canal can be caused by excessive earwax (cerumen) or foreign objects such as beads, beans or bugs. Infections of the ears include otitis externa (swimmer's ear), otitis media, an infection of the inner ear, mastoiditis and other pathologies as mentioned above and fully described in the literature. Other disorders that may cause ear pain are allergic reactions, ruptured eardrum, acute sinusitis, chronic sinusitis, tooth abscess, sore throat with referred pain to the ears, Meniere's disease, tumors of the ear, which may be cancerous or benign and temporomandibular joint (jaw) syndrome.

Currently available analgesic ear drops used for the treatment of ear pain usually contain an analgesic compound such as: benzocaine, tetracaine, amethocaine antipyrine and/or phenazone.

Ear drops are usually administered to the treated ear by tilting the head of a treated subject to the side, instilling drops of the medicament into the ear and maintaining the adopted position for few minutes, in order to allow the medicine to reach the interior of the ear. A clean cotton-wool plug may be inserted into the opening of the ear to prevent the medication from leaking out. In addition, in order to prevent contamination of the ear drops, the bottle tip must not be in contact with any surface, including the hands and the ear itself.

A number of drawbacks are associated with ototopical administration in the form of drops. In principle, ear drops exert their effect by direct contact with the affected area. If administration is poor (e.g., the head of the treated subject is not tilted long enough) and the drops cannot reach the infected area, the active agent cannot be effective. Delivery can be impaired in a number of different ways, including failure of the drops to enter the ear canal, short contact period of the medicament with the ear canal since the drops are naturally washed out or because the head of the treated subject is not tilted long enough for the agent to reach its target. In addition, the form of the current medicaments as ear drops is difficult to apply, especially to small children and animals that tend not to cooperate mainly due to the difficulty in maintaining a sedentary position for a prolonged period (several minutes). Cotton wool, that is usually added to the ear after administering the drops, might be pushed inside the ear canal and is difficult to remove. Also, the existing drugs often inadequately address a patient's needs for efficacy and aesthetics (e.g. running of drops on face and neck), and the failure to address those needs may decrease patient compliance and impair overall treatment.

Attempts have been made to provide alternate devices and methods for delivery of medication to the ear canal. U.S. Pat. No. 6,764,470 teaches an ear plug medication administration device that maintains the medication in the ear canal. The device comprises a resilient casing comprising a barrier defining an enclosed reservoir for a medication. The casing is configured to be compressed to fit within the ear, and configured to eject the medication upon being compressed. This device requires considerable handling and is awkward for use with infants and children.

U.S. Pat. No. 4,241,048 discloses anesthetic compositions comprising a therapeutically effective amount of powdered Benzocaine. In particular embodiments, the composition is in the form of a foamable liquid, aerosol product or a solid. In the disclosure, it is noted that the compositions ".can also be applied to burns, sunburn, poison ivy, insect bite, otic (ear), teething (gums) preparations, etc."

US patent application publication number 20020064541, and U.S. Pat. Nos. 5,744,166 6,238,650 are directed to compositions for topical application in the form of microcapsules or microspheres.

The above disclosures neither teach nor suggest a composition or use of a foam or mousse to treat ear disorders.
Foam Delivery of Therapeutic Agents Various foams useful for the delivery of therapeutic agents to the skin and body cavities are taught in the art. U.S. Pat. No. 6,730,288 discloses aerosol foam, also referred to as "mousse", for topical administration of insoluble pharmaceutically active ingredients. The composition comprises an occlusive agent in an amount sufficient to form an occlusive layer on the skin. Administration of mousse to the ear is neither taught nor suggested.

International patent application publication WO 2004/037225 teaches alcohol-free cosmetic or pharmaceutical foams suitable for delivery of both water soluble and oil-soluble pharmaceutical agents. That patent teaches foams useful for topical application of pharmaceutical agents to body cavities.

U.S. Pat. No. 4,915,934 teaches a quick-breaking foamable biocidal composition, comprising a quick breaking alcoholic foaming agent comprising: an aliphatic alcohol, a fatty alcohol, water and a surface-active agent.

U.S. Pat. No. 5,759,520 discloses a method for treating conditions of the gastro-intestinal tract, comprising administering from a pressurized container an aqueous foamable composition comprising a major amount by weight of water; a foaming agent consisting of a water-immiscible liquified gas; at least one emulsifying surfactant; Xanthan gum; and an effective amount of a pharmaceutically active substance; the composition having a delayed foaming action.

U.S. Pat. No. 6,126,920 teaches methods of treating various skin diseases, including scalp psoriasis, utilizing a foamable pharmaceutical composition comprising a corticosteroid active substance, a quick-break foaming agent, a propellant and a buffering agent. The present invention is preferably intended to increase the residence time of a pharmaceutical composition in the ear, and does not preferentially use quick breaking foams.

U.S. Pat. Nos. 5,393,528 and 5,529,782 teach a device comprising a dissolvable film made of polyvinyl alcohol, polyethylene oxide, hydroxypropylmethyl cellulose and mixtures thereof and a method for the delivery of medication. Nitrogen gas may be introduced while mixing to form frothy foam. Those patents do not disclose administration of foam into a bodily cavity.

UK Patent GB0933486 teaches liquid non-aqueous foamable aerosol compositions and provides a general disclosure of stable foams. That disclosure mentions in passing that "a quick breaking foam may be required for applying a uniform coating of a non-aqueous liquid to an irregular or inaccessible surface such as the middle ear" but neither teaches nor suggests compositions for the treatment of ear disorders or methods of administering a composition to the outer ear, which is the more appropriate method of application.

U.S. Pat. No. 6,521,213 teaches a method for preventing otitis externa by administering an aerosolized mixture of lipid crystals to the epithelial lining of the external auditory canal. The patent further teaches a method of treating otitis externa by administering a mixture of lipid crystals further comprising a therapeutic agent. The present invention does not use lipid crystals.

U.S. Pat. No. 4,305,936 relates to a composition comprising at least one corticosteroid, for topical or local application to the skin or body cavity. According to one embodiment of that patent, the preparation can produce a foam when packaged in the form of an aerosol or non-aerosol foam-forming closure system.

None of the above disclosures teach or suggest the delivery of medicaments specifically to the ear in the form of a foam or mousse.

Thus, there is a widely recognized need for, and it would be highly advantageous to have convenient and practical forms of medicaments to treat ear disorders, that ma overcome all drawbacks related to the use of such medicaments in the form of drops.

SUMMARY OF THE INVENTION

The present invention provides novel delivery systems for providing a medicament for the treatment of ear disorders in general, and of outer ear and middle ear disorders in particular. Specifically, the present invention provides compositions and methods for treatment of an ear disorder in a subject, the methods comprising administering a pharmaceutical composition in the form of a foam or mousse through the external auditory meatus (EAM) of the subject.

According to the principles of the present invention the formulation and administration of such a medicament into the ear is in a form selected from a foam or mousse.

The application of a medicament in these forms allows prolonged contact of the active agent/s with the surface of the ear canal, and therefore enables non-frequent applications (e.g. once or twice a day only). The prolonged contact of the active agent/s with the affected area further facilitates rapid healing compared to the conventional treatment with ear drops. Furthermore, administration of such forms into the ear is much more convenient than the administration of drops or insertion of a device, and makes it completely unnecessary either to tilt the head of a treated subject to the side during administration of the medicament, or to plug the ear meatus with a cotton-wool or other plug, in order to prevent the medication from leaking out. Additionally, administration of foam or mousse into the ear may be used to provide a measured dose of medicament to the ear.

In one aspect the present invention provides a pharmaceutical composition for the treatment of an ear disorder in a form selected from foam and mousse comprising:

a) at least one pharmaceutical agent known to affect an ear disorder;

b) a pharmaceutically acceptable carrier comprising at least one dispersing agent that is a foam forming agent; and c) a dispensing device adapted for the dispensing the pharmaceutical agent of a) admixed with the agent of b) to the external auditory meatus in a form selected from a foam and a mousse.

In certain embodiments the dispersing agent that is a foam forming agent is selected from a surfactant, a cholesteryl ester, a fatty acid, a phospholipid, a carbohydrate and a protein.

In certain embodiments the pharmaceutical composition is provided as an aerosol foam or mousse and the composition further comprises a propellant. The propellant used may be chosen from conventional aerosol propellants. Thus, the propellant may be selected from propane, butane, dichloro difluoro methane, dichloro tetrafluoro ethane, octafluoro cyclobutane, and mixtures of two or more thereof. The propellant may be present in amounts of about 3 to about 30% w/w.

In other embodiments the composition is provided as non-aerosol foam or mousse.

In certain embodiments of the present invention, the pharmaceutical composition is administered to the treated subject in a dispensing device that provides a metered dose and an otic adaptor adapted to administer the composition at or through the external auditory meatus. Preferably each metered dose of the composition provides an acceptable therapeutic dose in a final volume, which is suitable to fill the external auditory canal of the treated subject.

In some embodiments the ear disorder is selected from an external ear disorder, a middle ear disorder and an inner ear disorder. In other embodiments the external ear disorder or diseases is selected from those resulting from infection, allergy, trauma and cysts and tumors and include in a non-limiting manner otitis externa ("Swimmer's Ear"), necrotizing external otitis, otomycosis, perichondritis, bullous myringitis, herpes zoster oticus (Ramsey Hunt Syndrome), contact dermatitis, ear eczema, lacerations of the external canal, presence of foreign bodies, pilar (sebaceous) cysts, epidermal cysts, benign lesions including exostosis and malignant lesions including basal cell epithelioma and squamous cell carcinoma. According to specific embodiments the external ear disorder is selected from otitis externa, acute otitis externa and suppurative otitis externa.

In other embodiments the middle ear disorder and disease is selected from those resulting from infection, trauma and tumors including otitis media, chronic otitis media, serous otitis media (otitis media with effusion) acute and chronic suppurative otitis media, acute and chronic mastoiditis, adenoid hypertrophy, neoplasia, intratubal obstruction, middle ear obstruction, perforation of the eardrum (tympanic membrane), cholesteatoma (congenital, primary acquired, secondary acquired), tympanosclerosis, temporal bone fractures, barotrauma, glomus tumors and malignant neoplasia including squamous cell carcinoma. In one embodiment the ear disorder is a middle ear disorder selected from acute otitis media, suppurative otitis media and mastoiditis.

In specific embodiments the symptoms of middle ear pathology are selected from otalgia, tinnitus, and hearing loss. The etiology may be a direct disorder or disease of the middle ear or may result from referred pain.

In other embodiments the disorders and diseases of the ear are selected from otalgia caused by any physical or biological cause including without limiting: blockages, barotraumas, allergic reactions, acute sinusitis, chronic sinusitis, tooth abscess, sore throat with referred pain to the ears, Meniere's disease, myringitis, tumors, temporomandibular joint syndrome, temporal bone fracture and any other condition that requires administration of any kind of medicament into the ear canal of a treated subject in particular.

In some embodiments the ear disease or disorder is an inner ear disorder including symptoms of Meniere's disease, which may be treated by administering the composition of the present invention to the external and middle ear.

In specific embodiments the ear disorder is selected from an ear infection, an ear tumor and otalgia (ear pain).

In specific embodiments the ear disorder is otalgia, the otalgia caused by any physical, chemical or biological cause. In one embodiment the cause of otalgia is selected from a blockage, an external ear infection, a middle ear infection, an allergic reaction, a tooth abscess and an upper respiratory infection.

In certain embodiments of the current invention the pharmaceutical composition comprises a therapeutically effective amount of at least one of the following pharmaceutical agents selected from an antibacterial agent, an antibiotic agent, an anti-fungal agent, an antiviral agent, a steroid, an anti-inflammatory agent and an analgetic agent or a mixture thereof of at least two of such agents.

In one embodiment of the invention, the pharmaceutically active agent is an antibiotic agent. The antibiotic agent may be, for example, amikacin, gentamycin, tobramycin, streptomycin, netilmycin, kanamycin ciprofloxacin, norfloxacin, ofloxacin, trovafloxacin, lomefloxacin, levofloxacin, enoxacin, sulfonamides, polymyxin, chloramphenicol, neomycin, paramomomycin, colistimethate, bacitracin, vancomycin, tetracyclines, rifampins, cycloserine, beta-lactams, cephalosporins, and pharmaceutically acceptable derivatives thereof. In specific embodiments the pharmaceutical agent is an antibiotic selected from neomycin, ofloxacin and ciprofloxacin.

In some embodiments the pharmaceutically active agent is an antibacterial agent selected from zinc, acetic acid or boric acid or a mixture thereof.

In certain embodiments the pharmaceutically active agent is an anti-inflammatory agent selected from a non-steroidal anti-inflammatory drug (NSAID) and a steroid. The steroid may be selected from the group consisting of betamethasone, betamethasone dipropionate, fluocinonide, fluocinoline acetonide, hydrocortisone, methylprednisolone, clobetasol, beclomethasone, dexamethasone sodium phosphate, triamcinolone and pharmaceutically acceptable derivatives thereof. In specific embodiments the steroid is selected from hydrocortisone, betamethasone and dexamethasone.

In some embodiments the pharmaceutically active agent is an antifungal agent selected from the group consisting of amphotericins, fluconazole, flucytosine, natamycin, miconazole, ketoconazole, amphotericin B, nystatin, cromolyn, lodoxamide, levocabastine, naphazolin, antazoline, pheniramimane and pharmaceutically acceptable derivatives thereof.

In some embodiments the pharmaceutically active agent is a local anesthetic agent selected from the group consisting of benzocaine, benzyl benzoate, bupivacaine, calamine, chloroprocaine, chloroxylenol, cinchocaine, cocaine, dexivacaine, diamocaine, dibucaine, dyclonine, etidocaine, hexylcaine, ketamine, levobupivacaine, lidocaine, menthol, mepivacaine, oxethazaine, phenol, pramoxine, prilocalne, amethocaine, tetracaine, proparacaine, propoxycaine, pyrrocaine, resorcinol, risocaine, rodocaine, ropivacaine, tetracaine, and pharmaceutically acceptable derivatives thereof. In specific embodiments the pharmaceutical agent is an analgetic selected from anti-pyrine, lidocaine and derivatives thereof.

In certain embodiments the pharmaceutical composition comprises more than one pharmaceutically active agent. In specific embodiments the medicament comprises neomycin, polymyxin B and hydrocortisone. In other embodiments the pharmaceutical composition comprises chloroxylenol (halogenated phenol), pramoxine hydrochloride and hydrocortisone.

It is explicitly understood that the pharmaceutical composition and methods of the present invention are suitable for pharmacologically active agents, whether water soluble, poorly water soluble or water insoluble. In certain embodiments the pharmaceutically active agent is neither soluble in aqueous carriers nor in a lipid carrier. The judicious choice of ingredients will allow foam delivery whether the active ingredients are water-soluble or not. Combinations of active ingredients that are individually and independently water soluble or insoluble may also be practiced according to the present invention. There are many available solutions to the problem of formulation of poorly soluble ingredients for improved drug bioavailability including the use of surfactants, micelle solutions, emulsions, microemulsions and organic cosolvents, as are well known in the art of pharmaceutical formulations.

In some embodiments the pharmaceutically acceptable carrier is a hydrophilic carrier. In certain embodiments the composition of the present invention is an aqueous based foam. In some embodiments the composition comprises an oil-in-water emulsion, or microemulsion.

In other some embodiments the pharmaceutically acceptable carrier is a lipophilic carrier. In certain embodiments the composition is a lipid-based mousse. In some embodiments the composition comprises a water-in-oil emulsion.

According to various embodiments the at least one dispersing agent that is a foam forming agent is selected from the group consisting of natural or synthetic agents including a surfactant, a cholesteryl esters, a fatty acid, a phospholipid, a carbohydrate, and a protein. In certain embodiments the pharmaceutically acceptable carrier further comprises at least one surfactant selected from a natural or synthetic ionic or non-ionic surfactant or mixture thereof.

The pharmaceutical composition provided by the present invention, may be administered to the ear of the treated subject through a device in which the compositions are packed under pressure, suitable for application to the treated are in a form selected from a foam or mousse. In one preferred embodiment the dispensing device is selected from an aerosol dispensing device and a non-aerosol dispensing device. According to another aspect the present invention provides a device or apparatus for administration of a medicament to the ear of a subject in the form of a foam or mousse comprising a container comprising the pharmaceutical composition and an extension, typically a tube extending therefrom, said extension adapted to access the outer ear in a convenient and gentle manner. Preferably, the medicament is formulated as a foamable composition, which, upon admixing with a gas propellant in an aerosol container, produces a foamable composition that is suitable for administration to the external auditory meatus (ear canal). Alternatively the foamable composition is administered using a non-aerosol dispenser.

According to another aspect the present invention provides a method for the treatment of an ear disorder in a subject in need thereof comprising administering an amount of a pharmaceutical composition in a form selected from foam and mousse through the external auditory meatus of said subject so as to thereby treat the ear disorder.

In another aspect the present invention further provides a method of preparing a pharmaceutical composition for the treatment of an ear disorder in the form selected from a foam and a mousse, the method comprising the steps of:

a) providing a pharmaceutical agent known to affect an ear disorder;

b) admixing the pharmaceutical agent of step (a) with a suitable pharmaceutically acceptable carrier comprising at least one dispersing agent that is a foam forming agent; and c) introducing the mixture of (b) into a dispensing device adapted for the dispensing the composition to the external auditory meatus in the form selected from a foam or mousse.

In yet another aspect the present invention provides a method for the treatment of an ear disorder in a subject in need of such treatment, the method comprising the steps of:

a) providing a pharmaceutical agent known to affect an ear disorder;

b) admixing the pharmaceutical agent of step (a) together with a pharmaceutically acceptable carrier comprising at least one dispersing agent that is a foam forming agent;

c) introducing the mixture formulation of step (b) in a container that enables the dispersion of said mixture in a form selected from foam and mousse; and d) administering the formulation of step (c) to the external auditory meatus of said subject so as to thereby treat the ear disorder.

In one preferred embodiment of the invention, the pharmaceutical composition is administered to the treated subject in a dispensing device that provides a metered dose. Preferably each metered dose of the formulation provides an acceptable therapeutic dosage in a final volume, which is suitable to fill the ear canal of the treated subject.

The present invention further provides use of a pharmaceutical composition in a form selected from a foam and a mousse for the treatment of any ear disorder which requires administration of a pharmaceutical composition through the external auditory meatus of a treated subject, so as to thereby treat the ear disorder.

In specific embodiments the treated subject is a mammal, preferably a human. In other embodiments the mammal is a domestic animal.

These and further features of the present invention will be better understood in conjunction with the drawings, detailed description, examples and claims that follow.

DETAILED DESCRIPTION OF THE INVENTION

Figure 1:
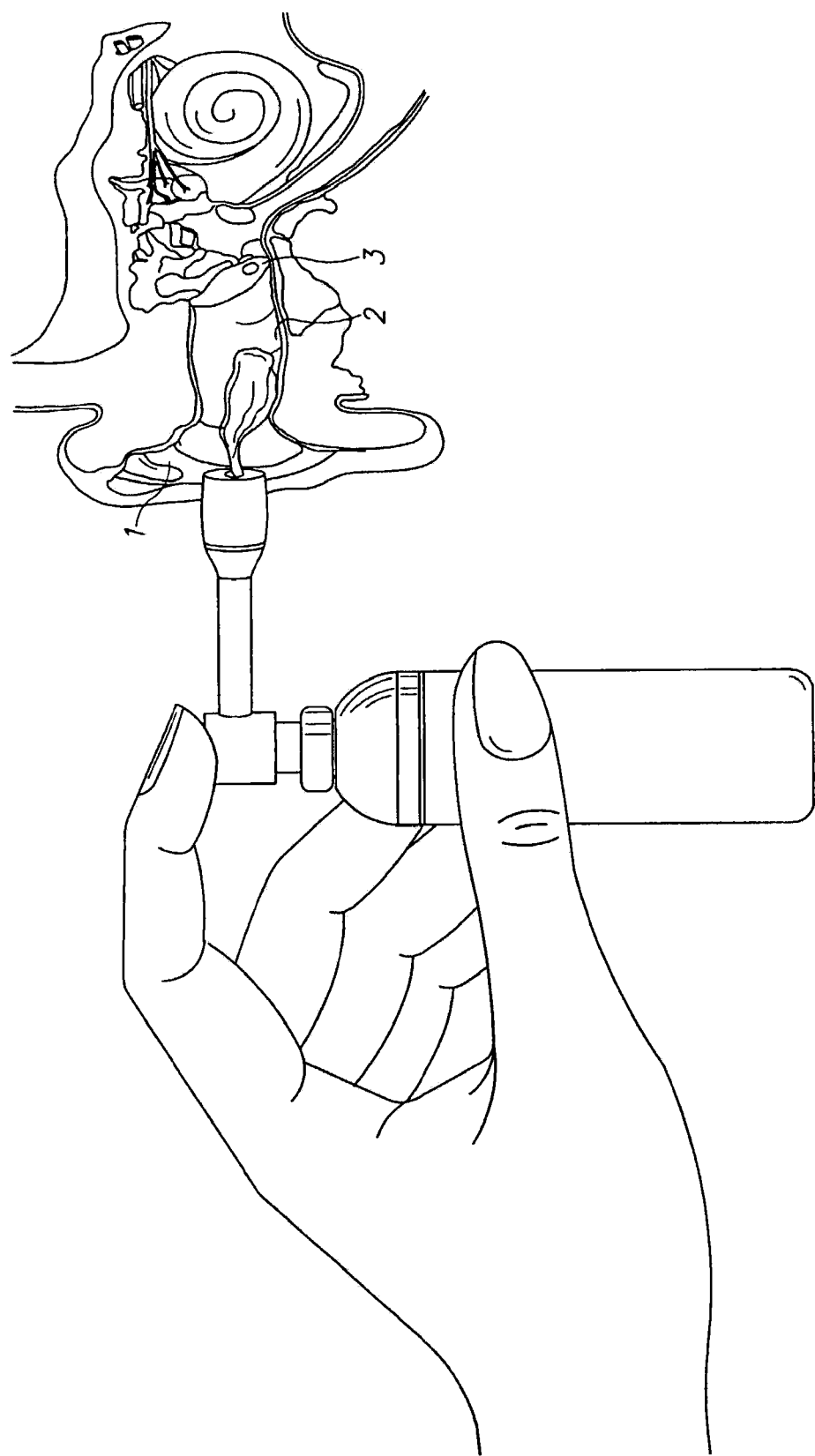
FIG. 1 represents a side view of one embodiment of the delivery of the pharmaceutical composition of the invention in the form of a foam or mousse to the ear canal. The figure is labeled as follows: (1) marks part of the outer ear, the auricle; (2) identifies the ear canal (external auditory meatus); (3) identifies the ear drum (tympanic membrane).

In accordance with the present invention, ear care medicaments in a foam-based formulation are provided. More specifically, the present invention provides a method for the treatment of ear disorder in a subject in need of such treatment comprising administering an amount of a pharmaceutical composition in a form of foam through the external auditory meatus of said subject so as to thereby treat the subject.

As used herein, the term "foam" or "mousse" is defined any lightweight material in cellular form which is made by introducing gas bubbles into a liquid phase.

As used herein, the term "foam forming agent" is meant to include foam producing agents and compounds that are able to generate a foamable composition when admixed with a liquid or gel composition. The foamable composition generates a foam within the dispensing device or upon dispensing from the dispensing device. In certain embodiments the present invention provides a stable foam, i.e. wherein breaking of the foam is delayed.

The foam base formulations as opposed to ear drops offer an improved compliancy, i.e. the foam form could be applied infrequently to the treated area (e.g. once/twice daily) instead of frequent applications of current available ear drops (2-6 times a day). The foam-based formulation provides an improved administration to the treated subject, especially to infants, children and animals, since foam does not require special position, such as head tilting for several minutes. Furthermore, formulation in the form of a foam enable improved delivery of the medicament, so as the foam evaporates spontaneously after pre-determined period of time (by formulation), out of the ear without dripping. In addition, when the foam is applied to the ear, it does not leave any residue, stains or odor after it dries. Moreover, the uniqueness of the foam formulation is that there is a relatively uniform concentration of active ingredients at every site of the foam surface; hence the contact area of the active ingredient within the ear canal is effectively increased. The foam formulation further enables the active therapeutic agent/s to contact rapidly the treated area with substantially 100% coverage, and can improve penetration into the affected area.

Among other advantages, use of a foam-based formulation avoids the need and dangers of a cotton plug or wick, thus it dispenses with the use of such cotton, which is uncomfortable and may lead to deep insertion of the cotton, and the need for a trained physician to pull it out. Another advantage is in the metered, or measured, dosing accompanied by the delivery device. A premeasured dose obviates the uncertainties associated with delivering the correct amount of medicament.

In one aspect the present invention provides a pharmaceutical composition for the treatment of an ear disorder in a form selected from foam and mousse comprising:

a. at least one pharmaceutical agent known to affect an ear disorder;

b. a pharmaceutically acceptable carrier comprising at least one foam forming agent;

c. a dispensing device adapted for the dispensing the agent of a) with the agent of b) to the external auditory meatus.

In one embodiment of the invention, the treated ear disorder is any condition that requires administration of any pharmaceutical composition into the ear canal of the treated subject, so as to thereby treat the ear disorder. Such conditions include without limiting otitis externa, including acute otitis externa, acute otitis media, chronic suppurative otitis media, infections of the inner ear, mastoiditis, perforation of the tympanic membrane, ruptured eardrum, otalgia caused by any physical or biological cause as detailed previously including without limiting: allergic reactions, acute sinusitis, chronic sinusitis, tooth abscess, sore throat with referred pain to the ears, Meniere's disease, tumors and temporomandibular joint syndrome.

In another embodiment, the pharmaceutical composition of the present invention is used to manufacture a medicament for the treatment of ear disorders, which is administered to the subject in need of such treatment in the form of foam or mousse.

Pharmaceutical Agents

In a further embodiment, the pharmaceutical composition of the present invention comprises at least one therapeutically active pharmaceutical agent.

As used herein, the term "pharmaceutical composition" or "medicament or "therapeutically active agent" or "active agent" or "agent", are all broadly used to mean any chemical or material that is desired to be applied, administered or used to treat ear disorders and can include, by way of illustration and not limitation, any substance which is capable of altering a biologic, physiologic and/or immunologic function, and also substances generally referred to as pharmacological agents and drugs, including antibiotic agents, antibacterial agents, antifungal agents, steroid agents, anti-inflammatory agents and local anesthetic agents. The invention is meant to include a pharmaceutical composition comprising at least one therapeutically active agent.

In one embodiment of the invention, the therapeutically active agent is an antibiotic agent. The antibiotic agent may be, for example, neomycin, amikacin, gentamycin, tobramycin, streptomycin, netilmycin, kanamycin ciprofloxacin, norfloxacin, ofloxacin, trovafloxacin, lomefloxacin, levofloxacin, enoxacin, sulfonamides, polymyxin, chloramphenicol, neomycin, paramomomycin, colistimethate, bacitracin, vancomycin, tetracyclines, rifampins, cycloserine, beta-lactams, cephalosporins, and pharmaceutically acceptable derivatives thereof. In specific embodiments the pharmaceutical agent is an antibiotic selected from neomycin, ofloxacin and ciprofloxacin.

In a different embodiment, the active agent used in the provided method is an antibacterial or bacteriostatic agent. Such antibacterial agent may be, for example, zinc, acetic acid or boric acid or a mixture thereof.

In yet, a different embodiment of the present invention, the active agent is a steroid or steroid derivative. Such a steroid includes without limiting betamethasone, betamethasone dipropionate, fluocinonide, fluocinoline acetonide, hydrocortisone, methylprednisolone, clobetasol, beclomethasone, dexamethasone sodium phosphate, triamcinolone and pharmaceutically acceptable derivatives thereof.

In one another embodiment, the therapeutically active agent is an antifungal agent. The antifungal agent may be selected from the group consisting of amphotericins, fluconazole, flucytosine, natamycin, miconazole, ketoconazole, amphotericin B, nystatin, cromolyn, lodoxamide, levocabastin, naphazolin, antazoline, pheniramine and pharmaceutically acceptable derivatives thereof.

In a further embodiment, the therapeutically active agent is an anti-inflammatory agent. Such an agent may be, for example, any non-steroidal anti-inflammatory agent (NSAID), antipyrin and pharmaceutically acceptable derivatives thereof. Examples of the non-steroidal anti-inflammatory drug (NSAID) which is advantageously administered by the formulations of this invention include salicylic acid derivatives, such as, for example, aspirin; heteroaryl acetic acids, such as, for example, tolmetin, diclofenac, ketorolac; arylpropionic acids, such as, for example, ibuprofen, naproxen, flurbiprofen, ketoprofen, fenoprofen, oxaprozin; anthranilic acids (fenamates), such as, for example, mefenamic acid, meclofenamic acid, flufenamic acid; enolic acids, such as, for example, oxicams (e.g., piroxicam, tenoxicam), pyrazolidinediones (e.g., phenylbutazone, oxyphenthatrazone); alkanones, such as, for example, nabumetone. Among these, especially preferred, based on the current level of knowledge in the pharmacological arts, are ibuprofen, diclofenac, ketorolac, naproxen, flurbiprofen, ketoprofen and piroxicam. More generally, however, any of the government approved NSAIDs, such as listed in, for example, the most current edition of The Merck Index, may be advantageously used.

In still, another embodiment of the invention, the active agent is a local anesthetic agent. Such agent may be selected, for example, from the group consisting of benzocaine, benzyl benzoate, bupivacaine, calamine, chloroprocaine, chloroxylenol, cinchocaine, cocaine, dexivacaine, diamocaine, dibucaine, dyclonine, etidocaine, hexylcaine, ketamine, levobupivacaine, lidocaine, menthol, mepivacaine, oxethazaine, phenol, pramoxine, prilocalne, amethocaine, tetracaine, proparacaine, propoxycaine, pyrrocaine, resorcinol, risocaine, rodocaine, ropivacaine, tetracaine, and pharmaceutically acceptable derivatives thereof. Compositions according to the present invention may comprise any conventional carriers, excipients or adjuvant used in pharmaceuticals, personal care formulations and compositions or veterinary formulations. These carriers, excipients and adjuvants include, but are not limited to the following:

Acidifying agents, such as, boric acid, acetic acid, glacial acetic acid, citric acid, fumaric acid, hydrochloric acid, diluted hydrochloric acid, malic acid, nitric acid, phosphoric acid, sulfuric acid and tartaric acid.

Alcohol denaturants, such as, denatonium benzoate, methyl isobutyl ketone and sucrose octacetate.

Alkalizing agents including ammonia solution, ammonium carbonate, diethanolamine, diisopropanolamine, potassium hydroxide, sodium bicarbonate, sodium borate, sodium carbonate, sodium hydroxide or trolamine.

Antimicrobial preservatives, such as, benzalkonium chloride, benzalkonium chloride solution, benzelthonium chloride, benzoic acid, benzyl alcohol, butylparaben, acetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal and thymol.

Antioxidants, such as, ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, alpha tocopherol and other tocopherols and tocopherol derivatives.

Buffering Agents, including acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate and monobasic sodium phosphate.

Ointment Bases, including lanolin, anhydrous lanolin, hydrophilic ointment, white ointment, yellow ointment, polyethylene glycol ointment, petrolatum, hydrophilic petrolatum, white petrolatum, rose water ointment and squalane.

Plasticizers, e.g. castor oil, diacetylated monoglycerides, diethyl phthalate, glycerin, mono- and di-acetylated monoglycerides, polyethylene glycol, propylene glycol, triacetin and triethyl citrate.

Solvents, for example, acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation and purified water.

Sorbents, such as, powdered cellulose, charcoal, purified siliceous earth or carbon dioxide sorbents (e.g. barium hydroxide lime, soda lime).

Stiffening Agents, for example, hydrogenated castor oil, cetostearyl alcohol, cetyl alcohol, cetyl esters wax, hard fat, paraffin wax, polyethylene excipient, stearyl alcohol, emulsifying wax, white wax and yellow wax.

Suspending and/or Viscosity-increasing agents and adjuvants for a foamable liquid or gel base including, acacia, agar, alginic acid, aluminum monostearate, bentonite, purified bentonite, magma bentonite, carbomer 940 or 980, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, polyoxyethylene-polyoxypropylene-block polymers, hydroxypropyl methylcellulose, magnesium aluminum silicate, methylcellulose, pectin, polyethylene oxide, polyethylene glycol, wood wax, alcohols, polyvinyl alcohol, povidone, propylene glycol alginate, silicon dioxide, colloidal silicon dioxide, sodium alginate, tragacanth and xanthan gum, cocoa butter, hard fat and polyethylene glycol.

Agents that promote penetration, including urea, non-ionic detergents e.g. NP-40, Triton X-100, ionic detergents such as sodium dodecyl sulphate, lauryl decyl sulphate and chaotrophic salts.

Foam and Mousse Compositions

The pharmaceutical compositions of the present invention, as well as medicaments prepared by using these compositions may be altered into the form of a foam or mousse by any method known in the art for producing foam or mousse. For detailed description of such methods see for example: US Patent applications 20040057922; 20020018812 and U.S. Pat. Nos. 6,730,288; 5,369,131, International patent application publication WO 2004/037225 all incorporated herein by reference. In some embodiments the foamable composition, when placed in an aerosol container and combined with a liquefied gas propellant, releases a therapeutically beneficial foam or mousse product. In other embodiments the composition may be formulated as non-aerosol foam, for example in a propellant free dispenser.

Figure 2:
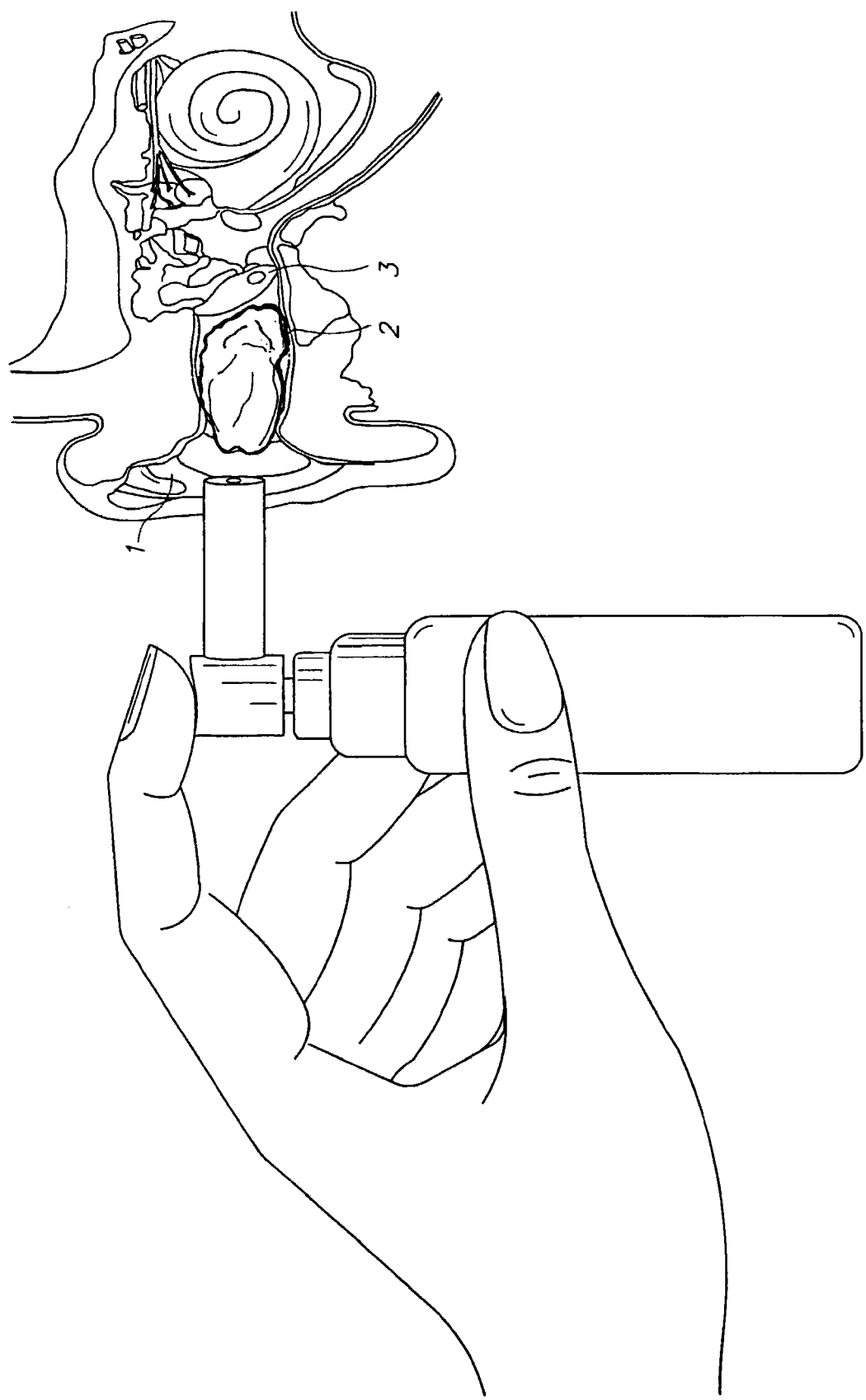
FIG. 2 represents a side view of one embodiment of a delivery device for providing a metered dose of a pharmaceutical composition of the invention. (1) marks part of the outer ear, the auricle; (2) illustrates a metered dose of foam or mousse following administration into the ear canal (external auditory meatus); (3) identifies the ear drum (tympanic membrane).

The pharmaceutical compositions provided by the present invention, may be administered to the ear of the treated subject through a device in which the compositions would be packed under pressure, prepared to be applied to the treated object in a form of foam, through an extension, nozzle or tube, said extension adjusted to access the outer ear in an easy and user friendly manner (FIGS. 1 and 2).

In one embodiment, the foam is ejected through an actuator that is elongated a few centimeters with a narrow stem-like part, which ends in a rounded and wider orifice, which prevents entry into and injury of the ear canal. In light of the wider and rounded tip of the stem, it is difficult, if not impossible to insert it deep into the ear canal. When the foam is ejected into the ear canal it expands and fills the whole ear canal, therefore it contacts with the whole ear canal area. This has many advantages since it enables contact of the active compound (pharmaceutical) for extended periods of time with the walls of the ear canal and therefore exerts its effect. FIGS. 1 and 2 illustrate non-limiting example of a device for the administration of the composition of the present invention. In FIG. 1, the parts of the ear are as follows: (1) marks part of the outer ear (auricle); (2) identifies the ear canal (external auditory meatus); (3) identifies the eardrum (tympanic membrane).

According to one preferred embodiment the foam is ejected from a dispensing device in a measured or metered amount. A metered dose is illustrated in FIG. 2. In FIG. 2, (2) illustrates a non-limiting example of a measured dose of foam or mousse in the ear canal, following administration.

In one another embodiment, the device is an aerosol device. As used herein, the term "aerosol" is directed to a container that contains a liquid with gas under pressure for dispensing said liquid as foam. The use of aerosol device is well known in the art to produce foam. An aerosol dispensing device is composed of a standard aerosol can (such as aluminum or tinplate), which can contain pressure higher than the atmospheric pressure. In the aerosol there is usually a liquid or gel in mono-phasic solution (i.e. homogeneous solution) or in bi-phasic solution (i.e. aqueous solution and oil solution). The container is tightly closed with a valve orifice. Thereafter a propellant (i.e. a liquefied gas) such as butane, propane or any other propellant as is known in the art is inserted, which creates the pressure inside the container. The way in which a product is dispensed as foam (mousse or gel) is directly influenced by the mixture of the product solution, propellant type and the technical design of the aerosol valve and actuator. Inside the container there is high pressure, (e.g. 3 atmospheres), and when the container is shaken, even minimally, the gas and liquid or liquids are mixed. Further description of aerosol devices and the creation of foam and dispersion processes are disclosed by way of example in U.S. Pat. Nos. 5,322,683; 5,397,564; and 6,730,288 all of which incorporated herein by reference.

In other embodiments the composition is administered as a foam or mousse using a non-aerosol device. Non-aerosol may be advantageous for certain compositions and non-aerosol dispensers are known in the art as disclosed by way of example in U.S. Pat. Nos. 5,635,469; 6,612,468; 6,660,282; and 6,030,931 all of which incorporated herein by reference.

U.S. Pat. No. 6,030,931 describes a non-aerosol pump foaming composition free of water insoluble emollients. Transparent systems achieve a luxurious foam generated through use of select amphoteric surfactants and densifying agents. Another non-limiting example of non-aerosol foam dispenser is disclosed in U.S. Pat. No. D456,260

It is explicitly understood that the pharmaceutical composition and methods of the present invention are suitable for pharmacologically active agents whether water soluble, poorly water soluble or water insoluble. The judicious choice of ingredients will allow the use of a foam delivery whether or not active ingredients are water soluble or not. Combinations of active ingredients that are water soluble or insoluble may also be practiced according to the present invention. There are many solutions to the problem of formulation of poorly soluble ingredients for improved drug bioavailability including the use of surfactants, micelle solutions, emulsions, microemulsions and organic cosolvents, as are well known in the art of pharmaceutical formulations.

In some embodiments the pharmaceutically acceptable carrier is a hydrophilic carrier. In certain embodiments the composition of the present invention is an aqueous based foam. In some embodiments the composition comprises an oil-in-water emulsion, or microemulsion.

In other some embodiments the pharmaceutically acceptable carrier is a lipophilic carrier. In certain embodiments the composition is a lipid-based mousse. In some embodiments the composition comprises a water-in-oil emulsion. In certain embodiments the lipid is selected from a synthetic lipid, a semi-synthetic lipid and a natural lipid.

The composition of the present invention comprises a pharmaceutical carrier comprising at least one dispersing agent that is a foam forming agent. The dispersing agent may be selected form at least one pharmaceutically acceptable surfactant selected from anionic, cationic, nonionic, zwitterionic, amphoteric and ampholytic surfactants, as well as mixtures of these surfactants. Nonlimiting examples of possible surfactants include polysorbates, such as polyoxyethylene (20) sorbitan monostearate (polysorbate 60); Polyoxyethylene (20) sorbitan monolaurate (polysorbate 20); polyoxyethylene (20) sorbitan monooleate (polysorbate 80); fatty acid esters, such as Myrj 45, Myrj 49 and Myrj 59; poly(oxyethylene) alkylyl ethers, such as poly(oxyethylene) cetyl ether, poly(oxyethylene) palmityl ether, polyethylene oxide hexadecyl ether, polyethylene glycol cetyl ether, brij 38, brij 52, brij 56 and brij W1; sucrose esters, partial esters of sorbitol and its anhydrides, such as sorbitan monolaurate; mono or diglycerides, isoceteth-20, sodium methylcocoyl taurate, sodium methyl oleoyl taurate, triethanolamine lauryl sulfate and betaines.

Other useful surfactants include alkali metal long-chain alkylsulfates, where the alkyl group has 9 to 15 carbon atoms, sodium lauryl sulfate (SLS), sodium dodecylbenzene sulfonate, sodium cocomonoglyceride sulfonate, sodium lauroylsarcosinate, and the like, potassium and triethanolammonium sulfates, sulfonates and sarcosinates. Among the nonionic and amphoteric surfactants useful herein preferred are those selected from the group consisting of lauryl polyglucoside, decyl polyglucoside, coconut alkyl N-methyl glucose amide, oleyl betaine, cocamidopropyl betaine, cocamidopropyl hydroxysultaine, sodium lauryl sarcosinate, coamdiopropyl PG-dimonium chloride phosphate, ceteth-2, ceteth-6, steareth-2, steareth-6, PEG-2 stearate, PPG-10 glyceryl stearate, and mixtures thereof. More preferred are those selected from the group consisting of lauryl polyglucoside, decyl polyglucoside, oleyl betaine, cocamidopropyl betaine, cocamidopropyl hydroxysultaine, sodium lauryl sarcosinate, coamdiopropyl PG-dimonium chloride phosphate and mixtures thereof.

The anionic surfactants advantageously employed in the composition of the present invention included poloxamers (poly(oxyethylene)-poly(oxypropylene) block copolymers).

Other foam forming agents include fatty alcohols having 12 or more carbons in their carbon chain, such as cetyl alcohol and stearyl alcohol, arachidyl alcohol, behenyl alcohol, 1-triacontanol, and fatty alcohols with longer carbon chains.

In certain embodiments of the present invention, the foam forming agent is a fatty acid having 16 or more carbons in its carbon chain, and is selected from hexadecanoic acid, stearic acid, arachidic acid, behenic acid, octacosanoic acid, and fatty acids having longer carbon chains or mixtures thereof.

In some embodiments of the present invention the foam forming agent comprises a mixture of fatty alcohols, fatty acids and hydroxy fatty acids and derivatives thereof in any proportion.

In one currently preferred embodiment of the invention, the pharmaceutical composition of the present invention is administered to the treated subject in a metered dose manner. The aerosol formulation is preferably arranged so that each metered dose or "puff" of aerosol will ejaculate a pre-determined volume of foam that would fill the ear canal. The advantage of the metered dose method is that the foam will not spill or reach beyond the ear canal, and a precise amount of the medicament is inserted.

In a preferred embodiment, an amount of about 0.1 cc to about 2.0 cc of aerosol formulation is ejaculated per actuation. More preferably, an amount of about 0.2 to about 1 cc of aerosol formulation is ejaculated per actuation of the device. The ejaculated amount is determined according to the age of the treated subject, which affects the volume of the ear canal. For example, the ear canal volume of a newborn baby to a one-month old infant is usually around 0.2 cc, of a six month old infant is usually 0.5 cc and around 2.0 cc of children older than twenty-four months and adults.

The use of metered dose devices for different applications is well know in the art, and is described in details in U.S. Pat. Nos. 6,032,836; 5,697,532; 5,502,076; 6,702,155; US Patent Application 20030178022, all incorporated herein by reference.

In a different embodiment, the delivery device of the foam-based formulation of the invention may comprise two parts: one part serves as a container that stores the medicament formulation, and upon pressure the medicament is ejected into the ear, in a metered dose manner in the form of foam. The second part is an extension or tube that leads the foam toward the ear canal.

The subject, treated by the method of the present invention may be a mammalian. In a preferred embodiment, the treated subject is a human being. The method provided is applicable to any age and can be used to newborns as well as adults. In a different embodiment the treated subject is an animal, preferably a domestic mammal, including but not limited to household pets.

It is within the scope of the present invention, to use a pharmaceutical composition in the form of a foam for the treatment of any ear disorder which requires administration of pharmaceutical composition through the external auditory meatus of a treated subject, so as to thereby treat the subject. The ear disorder may include any of the abovementioned disorders.

The present invention is further directed to a pharmaceutical composition used for the treatment of ear disorder in a form of foam or mousse comprising as an active ingredient one or more antibiotic agent, antibacterial agent, antifungal agent, steroid agent, anti-inflammatory agent, local anesthetic agent or a mixture thereof, together with a pharmaceutically acceptable carrier.

Methods

The present invention also provides a process of preparing a pharmaceutical composition for the treatment of an ear disorder in a form of foam or mousse to thereby treat a subject in need of such treatment comprising:
a. providing a pharmaceutical agent known to affect an ear disorder; and
b. admixing the pharmaceutical agent of step (a) together with a pharmaceutically acceptable carrier comprising a dispersing agent that is a foam forming agent;
c. introducing the mixture of (b) into a dispensing device.

According to one embodiment the dispensing device is a non-aerosol dispensing device. According other embodiments the dispensing devise is an aerosol device.

The pharmaceutically acceptable carrier includes an aqueous carrier, a non-aqueous carrier or a mixture thereof, including oil-in-water emulsions ands water-in-oil emulsions.

The present invention further provides a method for treatment ear disorder in a subject in need of such treatment comprising:
a. providing a pharmaceutical agent known to affect an ear disorder;
b. admixing the pharmaceutical composition together with a pharmaceutically acceptable carrier comprising a dispersing agent that is a foam forming agent;
c. introducing the mixture in a container that enables the dispersion of said mixture in a form of foam; and
d. administering the formulation of step (c) to the external auditory meatus of said subject so as to thereby treat the subject.

In one embodiment of the invention, the pharmaceutical composition used for the treatment of ear disorder in the form of foam may comprise as an active ingredient at least one pharmaceutical agent selected from an antibiotic agent, an antibacterial agent, an antifungal agent, a steroid agent, an anti-inflammatory agent, a local anesthetic agent or a mixture thereof, together with a pharmaceutically acceptable carrier. The treated disorder by the disclosed method may be any of the abovementioned disorders.

In some embodiments the pharmaceutically acceptable carrier is selected from a hydrophilic carrier and a lipophilic carrier. In certain embodiments the pharmaceutically acceptable carrier further comprises a lipid surfactant. According to various embodiments the lipid surfactant and said dispersion agent of step (b) are selected from the group consisting of cholesteryl esters, phospholipids, carbohydrates, and proteins.

The foam is administered preferably in a metered dose. Each metered dose formulation contains an acceptable therapeutic dosage and ejaculates to a final volume, which is suitable to fill the ear canal of the treated subject. In a further embodiment, the pharmaceutical composition is used to manufacture a medicament.

During the production of the composition according to the present invention, a commonly used, a physiologically acceptable dispersion agent or stabilizer may be added. Non-limiting examples thereof include, propylene glycol, glycerine, polyethylene glycol, gelatin, dextran, polyvinylpyrrolidone, carboxymethyl cellulose, methyl cellulose, hydroxypropyl cellulose, sucrose fatty acid esters, polyoxyethylene hydrogenated castor oil, sterols, phospholipids, fatty acids, sugars, etc.

Furthermore the composition according to the present invention may contain physiologically acceptable additives as desired. For example, acceptable additives include antioxidants, antiseptics, stabilizers, isotonizing agents, buffering agents, etc. The required and optimum amounts of these substances may be varied depending on the object.

The following is a non-limiting description of diseases and disorders that may be amenable to treatment with the compositions and methods of the invention.

External Ear Disorders

The external ear is an area commonly subjected to acute and chronic inflammatory conditions. It consists of the auricle and external auditory meatus. The auricle is primarily composed of fibroelastic cartilage to which the skin and a small portion of subcutaneous tissue are attached, and of fat in the lobule. The external auditory meatus (EAM) is a skin-lined canal approximately 2.5 cm in length and ends medially at the tympanic membrane. Disorders of the outer ear include blockages, infections (external otitis and perichondritis), eczema, and tumors. The outer ear is also prone to certain types of injury. The Merck Manual, Second Home Edition, Chapter 219-220 Biology of the Ears, Nose, and Throat.

Blockages

Earwax (cerumen) may block the ear canal. Even large amounts of wax often produce no symptoms. Symptoms can range from itching to a loss of hearing. Other blockages can occur when people, particularly children, put foreign objects, such as beads, erasers, and beans, into the ear canal. Insects, particularly cockroaches, may also block the ear canal.

External Otitis

External otitis is infection of the ear canal. It may affect the entire canal, as in generalized external otitis, or just one small area, as in a boil (furuncle) or pimple. A variety of bacteria or, rarely, fungi can cause generalized external otitis. Certain people, including those who have allergies, psoriasis, eczema, or scalp dermatitis, are particularly prone to external otitis. Injuring the ear canal while cleaning it or getting water or irritants such as hair spray or hair dye in the canal often leads to external otitis. External otitis is particularly common after swimming in fresh water pools, in which case it is sometimes called "swimmer's ear". Earplugs and hearing aids make external otitis more likely, particularly if these devices are not properly cleaned.

Acute otitis externa (AOE) affects four in every thousand Americans annually (Hannley M T, Denneny J C, Holzer S S. Use of ototopical antibiotics in treating 3 common ear diseases. Otolaryngol Head Neck Surg 2000; 116:934-940), and is reported to be one of the leading causes of physician visits due to ear pain (LaRosa S. Primary Care Management of otitis externa. Nurse Pract 1998; 23:125-133).

Some risk factors associated with AOE include living in tropical or humid climates, summer season and swimmers or those who enjoy other water sports (Pelton S I, Klein J O. The draining ear. Otitis media and otitis externa. Infect Dis Clin North Am 1988; 2: 117-129; Biedlingmaier J F. Two ear problems you may not need to refer. Postgrad Med 1994; 96: 141-148). The warm and wet environment in the ear canal makes it an ideal location for bacteria to inhabit and proliferate. Additional risk factors as mentioned above, include insertion of foreign objects into the ear canal, accumulation of cerumen (earwax), hearing aids, and some skin conditions (seborrhea, psoriasis, or eczema) (Biedlingmaier J F. ibid., 1994). Foreign objects such as cotton-tipped swabs or anything used to clean the ear may damage and scratch the ear canal, making the area susceptible to infection. The buildup of earwax and the use of hearing aids may also decrease ventilation in the ear and keep the ear canal moist, thus leading to increased chances for developing AOE. Preventive measures to avoid the risk of AOE include keeping the ear canal clean and dry, using earplugs while swimming, avoiding cleaning or scratching ears with cotton-tipped swabs and avoiding shower heads with powerful streams of water directed to the ear canal (LaRosa S. Primary Care Management of otitis externa. Nurse Pract 1998; 23:125-133).

The most commonly isolated pathogens are *Pseudomonas aeruginosa* and *Staphylococcus aureus*. Other pathogens less commonly cultured include *Proteus mirabilis, Streptococci* species, coagulase negative *Staphylococci*, and various gram negative bacilli.

Symptoms of generalized external otitis are itching and pain. Sometimes an unpleasant-smelling white or yellow discharge drains from the ear. The ear canal may have no swelling, slight swelling, or in severe cases be swollen completely closed. If the ear canal swells or fills with pus and debris, hearing is impaired. Usually, the canal is tender and hurts if the external ear (pinna) is pulled or if pressure is placed on the fold of skin in front of the ear canal. To a doctor looking into the ear canal through an otoscope (a device for viewing the canal and eardrum), the skin of the canal appears red and swollen and may be littered with pus and debris.

The treatment of otitis externa involves frequent and through atraumatic cleansing of the canal, use of the appropriate topical antibiotics, and treatment of associated inflammation and pain. Topical treatments have the advantage of avoiding systemic side effects, enhancing patient compliance, and maximizing treatment outcomes.

Chronic Otitis Externa

Chronic otitis externa (COE) is an inflammatory process of the ear canal due to bacterial, fungal, or other dermatological disorders. COE can result from recurrent otitis externa, chronic purulent otitis media with perforation, or eczematoid dermatitis. The disease can be defined by having persistent symptoms for more than 2 months, which include unrelenting pruritus, mild discomfort, and dry flaky skin in the EAC. Multiagent topical treatments and frequent cleanings are often necessary. Topical application of steroids may help alleviate the chronic itching and resultant excoriations often present with this condition.

Otomycosis

Otomycosis is a fungal infection of the skin of the EAC. Fungi can be either the primary pathogen or superimposed on bacterial infections. The most common fungi implicated in otomycosis are *Aspergillus* and *Candida*. The usual symptoms of otomycosis are pruritis deep within the ear and an urge to scratch. Tinnitus is also a common presenting complaint. Treatment is directed at thorough cleaning and drying of the canal followed by the application of at least one topical antifungal medication.

Granular Myringitis

Granular Myringitis is the result of localized chronic inflammation of the lateral surface of the pars tensa of the tympanic membrane and is characterized by persistent, incompletely epithelialized granulation tissue over the involved area. Gram-negative bacilli are the most commonly cultured organisms, especially *Pseudomonas* and *Proteus* species. Treatment includes careful and frequent debridement of the ear with the application of topical antibiotics, occasionally combined with steroids.

Perichondritis

Perichondritis is infection of the cartilage of the external ear. Injury, burns, insect bites, ear piercing, or a boil on the ear may cause perichondritis. The infection also tends to occur in people whose immune system is weakened and in people who have diabetes. The first symptoms are redness, pain, swelling of the ear, and sometimes a fever. Pus accumulates between the cartilage and the layer of connective tissue around it (perichondrium). Sometimes the pus cuts off the blood supply to the cartilage, destroying it and leading eventually to a deformed ear. Although destructive and long-lasting, perichondritis tends to produce only mild discomfort.

Bullous Myringitis

This is a viral infection often confined to the tympanic membrane and primarily involves younger children. The presenting symptom is one of severe pain without fever and hearing loss. Treatment is aimed at pain relief and systemic and topical antibiotics to prevent secondary bacterial infection.

Tumors

Tumors of the ear may be noncancerous (benign) or cancerous (malignant). Noncancerous tumors may develop in the ear canal, blocking it and causing hearing loss and a buildup of earwax. Such tumors include small sacs filled with skin secretions (sebaceous cysts), osteomas (bone tumors), and growths of excess scar tissue after an injury (keloids). Basal cell and squamous cell cancers are common skin cancers that often develop on the external ear after repeated and prolonged exposure to the sun. Ceruminoma (cancer of the cells that produce earwax) develops in the outer third of the ear canal and can spread. Certain chemotherapeutic agents may be useful in treating or reducing the symptoms associated with these disorders.

Injury

A number of different injuries can affect the outer ear. A blunt blow to the external ear can cause bruising between the cartilage and the layer of connective tissue around it (perichondrium). When blood collects in this area, the external ear becomes swollen and purple. The collected blood (hematoma) can cut off the blood supply to the cartilage, allowing that portion of the cartilage to die, leading in time to a deformed ear. This deformity, called a cauliflower ear, is common among wrestlers, boxers, and rugby players. A forceful blow to the jaw may fracture the bones surrounding the ear canal and distort the canal's shape, often narrowing it.

Middle and Inner Ear Disorders

Middle and inner ear disorders produce many of the same symptoms, and a disorder of the middle ear may affect the inner ear and vice versa.

Acute Otitis Media

Acute otitis media is a bacterial or viral infection of the middle ear. Acute otitis media results from infection by viruses or bacteria, often as a complication of the common cold or of allergies. Acute otitis media is more common in children than in adults. The infected ear is painful, with a red, bulging eardrum. It is usually treated by antibiotics, such as amoxicillin. Acetaminophen or nonsteroidal anti-inflammatory drugs (NSAIDs) can relieve pain. Decongestants containing phenylephrine may help, and antihistamines are useful used for people who have allergies.

Occasionally acute otitis media is complicated with purulent discharge typically via ventilation tubes (in the ear drum) or via perforation in the ear drum, this condition is named suppurative otitis media which can be acute or chronic. Presently, suppurative otitis media is treated mainly with antibiotic ear drops.

Serous Otitis Media

Serous (secretory) otitis media is an accumulation of fluid in the middle ear. It can develop from acute otitis media that has not completely cleared or from a blocked eustachian tube. Allergies are a common cause of eustachian tube blockage. Serous otitis media can occur at any age but is particularly common in children.

Chronic Otitis

Chronic otitis media is a long-standing infection of the middle ear. It is caused by a permanent hole (perforation) in the eardrum or a noncancerous growth of white skin like material (cholesteatoma). People may have a perforation without ever getting any symptoms, but sometimes a chronic bacterial infection develops. Chronic otitis media may flare up after an infection of the nose and throat, such as the common cold, or after water enters the middle ear while bathing or swimming. Usually, flare-ups result in a painless discharge of pus, which may be malodorous, from the ear. Persistent flare-ups may result in the formation of protruding growths called polyps, which extend from the middle ear through the perforation and into the ear canal. Persistent infection can destroy parts of the ossicles, the small bones in the middle ear that connect the eardrum to the inner ear and conduct sounds from the outer ear to the inner ear, causing conductive hearing loss. Other serious complications include inflammation of the inner ear, facial paralysis, and brain infections. Some people with chronic otitis media develop cholesteatomas in the middle ear. Cholesteatomas, which destroy bone, greatly increase the likelihood of other serious complications.

Mastoiditis

Mastoiditis is a bacterial infection in the mastoid process, the prominent bone behind the ear. This disorder usually occurs when untreated or inadequately treated acute otitis media spreads from the middle ear into the surrounding bone, the mastoid process.

Perforation of the Eardrum

A perforation is a hole in the eardrum. A middle ear infection (otitis media) is the most common cause of eardrum perforation. The eardrum can also be perforated by a sudden change in pressure, either an increase, such as that caused by an explosion, a slap, or diving underwater, or a decrease, such as occurs while flying in an airplane. Another cause is burns from heat or chemicals. The eardrum may also be perforated (punctured) by objects placed in the ear, such as a cotton-tipped swab, or by objects entering the ear accidentally, such as a low-hanging twig or a thrown pencil. An object that penetrates the eardrum can dislocate or fracture the chain of small bones (ossicles) that connect the eardrum to the inner ear. Pieces of the broken ossicles or the object itself may even penetrate the inner ear. A blocked eustachian tube may lead to the perforation because of severe imbalance of pressure (barotrauma). Perforation of the eardrum causes sudden severe pain, sometimes followed by bleeding from the ear, hearing loss, and noise in the ear (tinnitus). The present invention further includes methods of treating this disorder.

Myringitis

Myringitis is infection of the eardrum caused by a variety of viruses and bacteria; the bacterium *Mycoplasma* is a common cause. The eardrum becomes inflamed, and small, fluid-filled blisters (vesicles) form on its surface. Blisters may also be present in otitis media; however, in myringitis, there is no pus or fluid in the middle ear.

Meniere's Disease

Meniere's disease is a disorder characterized by recurring attacks of disabling vertigo (a whirling sensation), hearing loss, and tinnitus. Meniere's disease is thought to be caused by an imbalance in the fluid that is normally present in the inner ear. This fluid is continually being secreted and reabsorbed, maintaining a constant amount. Either an increase in production of inner ear fluid or a decrease in its reabsorption results in an imbalance of fluid.

Temporal Bone Fracture

The temporal bone (the skull bone containing part of the ear canal, the middle ear, and the inner ear) can be fractured by a blow to the head. Temporal bone fractures frequently rupture the eardrum and may also damage the ossicles and the cochlea. Symptoms include facial paralysis on the side of the fracture and profound hearing loss, which may be conductive, sensorineural, or both.

Auditory Nerve Tumors

An auditory nerve tumor (acoustic neuroma, acoustic neurinoma, vestibular schwannoma, eighth nerve tumor) is a noncancerous (benign) tumor that originates in the cells that wrap around the auditory nerve (Schwann cells).

Barotrauma

Barotrauma is damage to the middle ear caused by unequal air pressure on the two sides of the eardrum.

EXAMPLES

The following non-limiting examples of compositions in accordance with the principles of the invention are provided for illustrative purposes only.

Example 1

Analgesic Ear Foam

Table 1 provides a non-limiting example of a composition of the present invention for administration of an analgesic to the ear.
Preparation Method:
A) The components 03, 04, and 02 are dissolved in 07 in the stated order in a stainless steel dissolving vessel of suitable capacity fitted with a propeller stirrer and turboemulsifier.
B) 05, 06 and finally 01 are added while stirring, and the turboemulsifier is then operated for 15 minutes.
C) Using a metering pump, the suspension is metered in the volume corresponding to the theoretical weight into aerosol cans while stirring.
D) Each can is immediately sealed by clinching the dispenser valve and is then pressurized by means of the propellant, which is fed in under pressure in a suitable quantity by a pumping device.

TABLE 1

| | COMPONENT | ACTIVITY | % COMPOSITION (of pressurized liquid) |
|---|---|---|---|
| 01 | antipyrin | active principle | 5 |
| 02 | tetracaine | active principle | 0.5 |
| 03 | Potassium metabisulphite | antioxidant | 0.25 |
| 04 | Sodium benzoate | antibacterial-anti-mildew agent | 0.3 |
| 05 | Polysorbate 20 | foaming surfactant | 4 |
| 06 | Polyglycol 300 isostearate | foam thickener | 4 |
| 07 | Purified water | | 75.87 |
| 08 | propellant | | 10 |

Example 2

Antibiotic Ear Foam

Foam compositions comprising at least one antibiotic agent are useful for the treatment of ear disorders indicating use of an antibiotic. A non-limiting example of a composition comprising antibiotic agents is presented in the table 2 herein below.

TABLE 2

| | COMPONENT | ACTIVITY | % COMPOSITION (of pressurized liquid) |
|---|---|---|---|
| 01 | Neomycin Polymyxin B Dexamethasone | active principles | 5 10,000 units/ml 1 |
| 02 | Xanthan gum | active principle thickener and suspension agent | 0.2 |
| 03 | Potassium metabisulphite | active principle antioxidant | 0.25 |
| 04 | EDTA bisodium salt | active principle antioxidant | 0.3 |
| 05 | Polysorbate 20 | foaming surfactant | 4 |
| 06 | Polyglycol 300 isostearate | foam thickener | 4 |
| 07 | Purified water | | 75.25 |
| 08 | propellant | | 6.5 |

Preparation Method:
A) The components 03, 04, and 02 are dissolved in 07 in the stated order in a stainless steel dissolving vessel of suitable capacity fitted with a propeller stirrer and turboemulsifier.
B) 05, 06 and finally 01 are added while stirring, and the turboemulsifier is then operated for 15 minutes.
C) Using a metering pump, the suspension is metered in the volume corresponding to the theoretical weight into aerosol cans while stirring.
D) Each can is immediately sealed by clinching the dispenser valve and is pressurized by means of the propellant, which is fed in under pressure in a suitable quantity by a pumping device

Example 3

Antibiotic Ear Foam 0.3% Ofloxacine

Table 3 provides an example of a composition of the present invention comprising a commonly administered antibiotic, ofloxacine.

TABLE 3

| | COMPONENT | ACTIVITY | % COMPOSITION (of pressurized liquid) |
|---|---|---|---|
| 01 | Ofloxacine | active principle | 0.3 |
| 02 | Dexamethasone | active principle steroid | 1.0 |
| 03 | Polysorbate 20 | foaming surfactant | 4 |
| 04 | Polyglycol 300 isostearate | foam thickener | 4 |
| 05 | Propyleneglycol | | 5 |
| 06 | Purified water | | 75.7 |
| 07 | propellant | | 10 |

Preparation Method:
A) The components 01 and 02 are dissolved in 06 in the stated order in a stainless steel dissolving vessel of suitable capacity fitted with a propeller stirrer and turboemulsifier.
B) 03, 04, 05 and finally 01 are added while stirring, and the turboemulsifier is then operated for 15 minutes.
C) Using a metering pump, the suspension is metered in the volume corresponding to the theoretical weight into aerosol cans while stirring.
D) Each can is immediately sealed by clinching the dispenser valve and is then pressurized by means of the propellant, which is fed in under pressure in a suitable quantity by a pumping device.

Example 4

Lipid-Based Mousse Formulations

Lipid based formulations are particularly useful for use with oil-soluble therapeutic agents. Non-limiting examples of such formulations are presented in table 4 herein below.

TABLE 4

|  | Example 4A | Example 4B | Example 4C | Example 4D |
|---|---|---|---|---|
| Petrolatum | 10-20% | 10-20% | 10-20% | 10-20% |
| Neomycin | 5% | | | |
| Polymyxin B | 10,000 u/ml | | | |
| Dexamethasone | 1% | 1% | | 1% |
| Tetracaine | | | 0.5% | |
| Antipyrine | | | 5% | |
| ciprofloxacine | | | | 0.2% |
| ofloxacine | | 0.3% | | |
| Alkyl benzoate | 10% | 10% | 10% | 10% |
| Sorbitan Stearate | 2.5-4.5% | 2.5-4.5% | 2.5-4.5% | 2.5-4.5% |
| Polysorbate 60 | 2.3-5.7% | 2.3-5.7% | 2.3-5.7% | 2.3-5.7% |
| Water | 20-75% | 20-75% | 20-75% | 20-75% |
| propellant | 5% | 5% | 5% | 5% |
| Total | 100% | 100% | 100% | 100% |

It will be appreciated by a person skilled in the art that the present invention is not limited by what has been particularly shown and described hereinabove. Rather, the scope of the invention is defined by the claims that follow.

The invention claimed is:

1. A method for the treatment of otitis externa, comprising administering into the ear canal of a subject in need of such treatment a pharmaceutical composition comprising an active agent capable of treating otitis externa, the pharmaceutical composition further comprising a foam forming agent, a hydrophilic carrier, and a propellant gas, said pharmaceutical composition being devoid of $C_1$-$C_4$ aliphatic alcohols and being formulated so as to form, upon ejection of said pharmaceutical composition from a dispensing device that includes a pressurized container and a pipe that extends from the pressurized container and allows access of the foam or mousse into the ear canal, an aqueous foam or mousse that provides prolonged contact of the active agent with the ear canal compared to the contact of said active agent with the ear canal when applied in the form of ear drops, wherein the pharmaceutical composition comprising the active agent is administered on a dosage schedule that is less frequent than would be required for administering said active agent in the form of ear drops.

2. The method according to claim 1, wherein the pharmaceutical composition is administered once a day.

3. The method according to claim 1, wherein the active agent is selected from the group consisting of an antibiotic agent, an antibacterial agent, an antifungal agent, a steroid agent, an analgesic agent and a mixture thereof.

4. The method according to claim 1, wherein the active agent is selected from the group consisting of neomycin, polymyxin B, ciprofloxacin, ofloxacin, oxytetracycline, nystatin, colistin sulfate, hydrocortisone, betamethasone, dexamethasone, benzocaine, amethocaine, and tetracaine.

5. The method according to claim 1, wherein the otitis externa is acute otitis externa.

6. The method according to claim 1, wherein the active agent is an antibiotic.

7. The method according to claim 1, wherein the active agent is an anti-inflammatory agent, an antibiotic, or a combination thereof.

8. The method according to claim 2, wherein the active agent is an antibiotic.

9. The method according to claim 2, wherein the active agent is an anti-inflammatory agent, an antibiotic, or a combination thereof.

10. A method for the treatment of otitis externa in a subject in need of such treatment, the method comprising the steps of:
    a) providing a pharmaceutical agent known to affect otitis externa;
    b) admixing the pharmaceutical agent of step (a) together with a pharmaceutically acceptable carrier being a hydrophilic carrier comprising at least one foam forming agent so as to form a mixture formulation, wherein said mixture formulation is devoid of $C_1$-$C_4$ aliphatic alcohols;
    c) introducing the mixture formulation of step (b) and a propellant gas into a container that enables the dispersion of said mixture and the propellant gas in a form selected from of an aqueous based foam and mousse when expelled from the container; and
    d) administering the formulation of step (c) to the auditory meatus of said subject in the form of an aqueous based foam or mousse which provides prolonged contact of the pharmaceutical agent with the ear canal compared to the contact of said pharmaceutical agent with the ear canal when applied in the form of ear drops so as to thereby treat the ear disorder, wherein the formulation comprising the pharmaceutical agent of step (c) is administered on a dosage schedule that is less frequent than would be required when administering said pharmaceutical agent in the form of ear drops.

11. The method according to claim 10, wherein the pharmaceutical agent is an antibiotic.

12. The method according to claim 10, wherein the pharmaceutical agent is an anti-inflammatory agent, an antibiotic, or a combination thereof.

13. A method for application of an antibiotic for the treatment of otitis externa, comprising administering into the ear of a subject in need of such treatment a pharmaceutical composition comprising an antibiotic, a foam forming agent, a hydrophilic carrier, and a propellant gas, the pharmaceutical composition being formulated so as to form, upon ejection of said pharmaceutical composition from a dispensing device that includes a pressurized container and a pipe that extends from the pressurized container and allows access of the foam or mousse into the ear, an aqueous based foam or mousse that provides prolonged contact of the antibiotic with the ear compared to the contact of said antibiotic with the ear when applied in the form of ear drops, wherein the pharmaceutical composition comprising the antibiotic is administered on a dosage schedule that is less frequent than would be required for administering said antibiotic in the form of ear drops.

* * * * *